United States Patent [19]

Buchwald et al.

[11] Patent Number: 4,657,530
[45] Date of Patent: Apr. 14, 1987

[54] COMPRESSION PUMP-CATHETER

[76] Inventors: Henry Buchwald, 100 Variety Club Heart Hospital, University of Minnesota, Minneapolis, Minn. 55455; Eugenio Guzman, 1730 Larpenteur Ave., Falcon Heights, Minn. 55113; Bruce D. Wigness, University of Minnesota, 2630 University Ave. SE., Minneapolis, Minn. 55455

[21] Appl. No.: 598,243

[22] Filed: Apr. 9, 1984

[51] Int. Cl.$^4$ ............................................. A61M 5/00
[52] U.S. Cl. ........................................ 604/9; 604/247
[58] Field of Search ............................. 604/8–10, 604/247, 185, 323, 264, 266, 268, 275, 276, 280

[56] References Cited

U.S. PATENT DOCUMENTS

| 3,109,429 | 11/1963 | Schwartz | 604/9 |
| 3,233,610 | 2/1966 | Wade | 604/9 |
| 3,492,996 | 2/1970 | Fountain | 604/9 |
| 3,566,875 | 3/1971 | Stoehr | 604/9 |
| 3,683,929 | 8/1972 | Holter | 604/9 |
| 3,910,283 | 10/1975 | Leveen | |
| 4,182,343 | 1/1980 | Inaba | 604/268 |
| 4,240,434 | 12/1980 | Newkirk | |
| 4,261,341 | 4/1981 | Hakim et al. | 604/9 |
| 4,346,704 | 8/1982 | Kulle | 604/247 |

Primary Examiner—C. Fred Rosenbaum
Assistant Examiner—Gene B. Kartchner
Attorney, Agent, or Firm—Burd, Bartz & Gutenkauf

[57] ABSTRACT

An ascites shunt is described in the form of an implantable, anti-reflux, fluid displacement, compression pump-catheter system. The system includes a double chambered multi-micro-orifice ascites collection device, an anti-reflux, anti-backdiffusion tubular compression pump, and an anti-reflux, anti-backdiffusion, non-thrombogenic catheter, all connected in series by flexible tubing. The shunt is used to transfer fluid from the peritoneum to a blood vessel to prevent accumulation of fluid within the peritoneal cavity. The pump and intravascular catheter include check valve tips of particular design to prevent both reflux and diffusion of blood components into the system.

9 Claims, 4 Drawing Figures

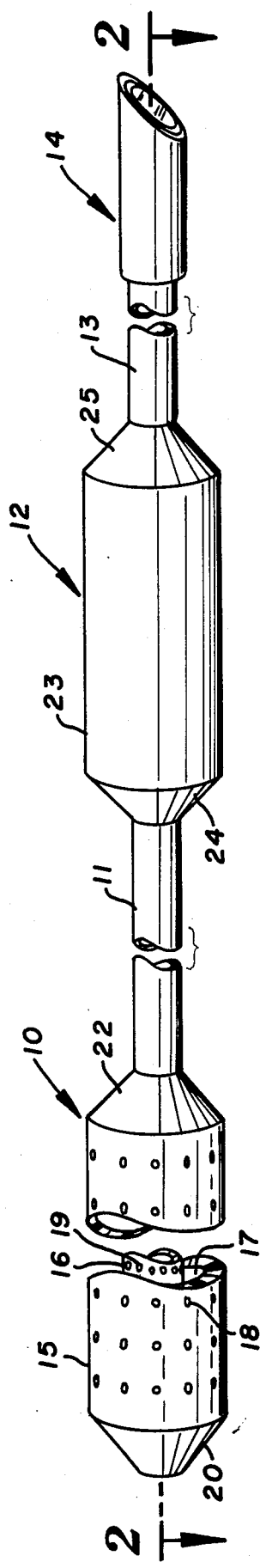
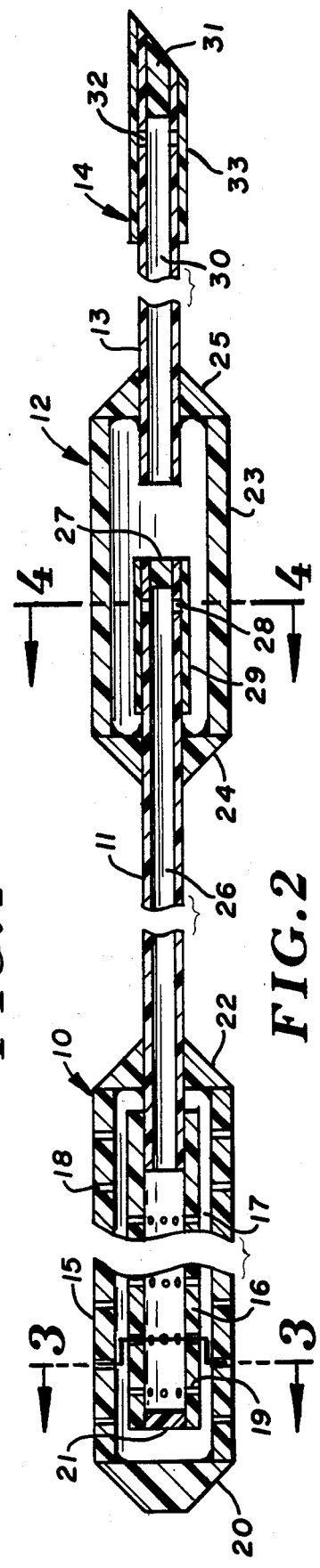
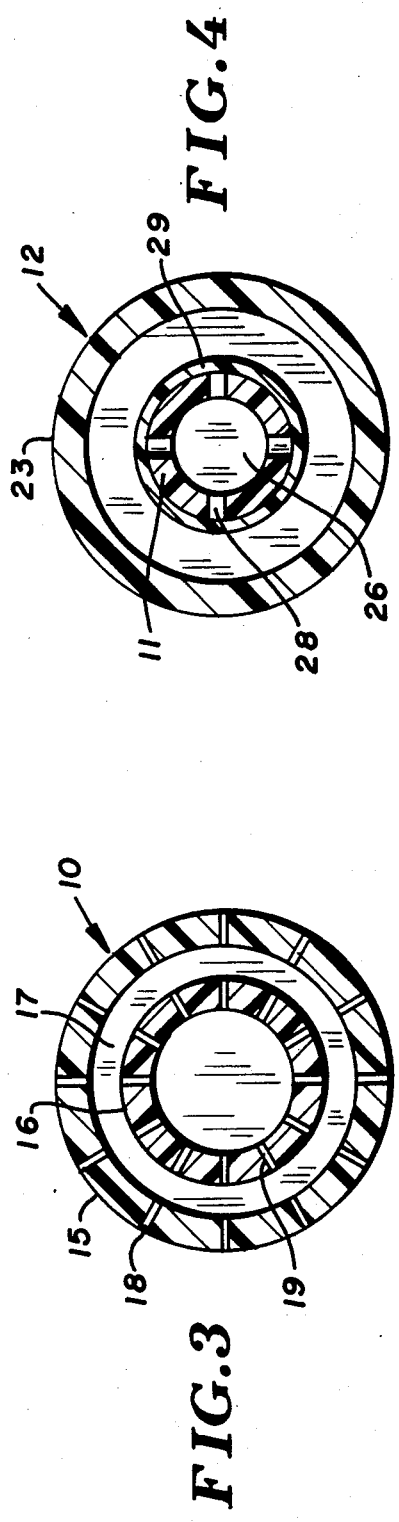

COMPRESSION PUMP-CATHETER

FIELD OF THE INVENTION
BACKGROUND OF THE INVENTION

This invention relates to an implantable anti-reflux fluid displacement compression pump-catheter used to transfer an unwanted accumulation of body fluids from a body cavity to a site where they can be processed by the body. The primary use for the pump-catheter is in the treatment of patients with ascites by the displacement of accumulated peritoneal cavity fluid into the systemic venous circulation.

The word "ascites" comes from the Greek word "askos" for bag. Hippocrates stated: "When the liver is full of fluid and this overflows into the peritoneal cavity so that the belly becomes full of fluid, death follows." Indeed, this is a very accurate description of the mechanism for ascites, as it is known today. There is evidence of the fact that ascites occurs with the obstruction, or increase in pressure, of hepatic lymphatics with a subsequent oozing of lymphatic fluid from the surface of the liver. If the fluid flux is high, especially in an individual with liver disease and portal venous system hypertension, there is inadequate re-absorption of this fluid and it accumulates within the peritoneal cavity.

Ascites pathophysiology, and the exchange of fluid between the peritoneal cavity and the various peritoneal surfaces, follows Starling's hypothesis. The pressure in the portal vein plus the oncotic pressure of the peritoneal fluid is the force that drives fluid from the intravascular space into the peritoneal cavity. This filtration force is opposed by the intraperitoneal hydrostatic pressure plus the plasma oncotic pressure. Since the liver capillaries are freely permeable to protein, any type of pressure imbalance of the above forces in favor of the production of peritoneal fluid leads to the formation of ascites.

In addition to the discomfort and pressure problems associated with massive abdominal distention due to ascites, patients with ascites are more prone to develop reflux esophagitis, respiratory failure, abdominal wall hernia defects, renal failure, and an increased susceptibility to infections.

The most frequent cause of ascites in the United States is cirrhosis of the liver, in 80 to 85% of the cases resulting from chronic alcoholism. According to the last U. S. census, there are believed to be approximately 600,000 ascitic individuals with alcoholic cirrhosis in this country.

In addition, there are other causes of ascites: chylous ascites, nephrogenic ascites, cardiogenic ascites, malignant ascites, and ascites due to other rare conditions. In other parts of the world, in particular in Asia, ascites is more often the result of liver disease due to parasitic infection.

In addition to its use in the management of ascites, the pump-catheter of this invention can, with modest modifications, be utilized for the transfer of other body fluids, e.g. the displacement of brain ventricular fluid in hydrocephalus to either the right atrium of the heart or to the peritoneal cavity.

THE PRIOR ART

Le Veen U.S. Pat. No. 3,910,283 discloses an apparatus for the continuous drainage of ascitic fluid from the peritoneum through a one-way valve into a silicone rubber tube which terminates in a jugular vein or other large vein for passage of the fluid into the vascular system. The valve body is made of polyethylene and the valve itself is made of silicone rubber, connected at each end to silicone rubber tubing. The diaphragm of the valve is held shut by the silicone rubber struts which yield to a pressure differential. While this design does not permit full flow from the cardiovascular system into the peritoneal cavity, diffusion into the catheter tip is not excluded.

Newkirk U.S. Pat. No. 4,240,434 discloses a similar device called the Denver shunt. In this device, a miter valve is contained in a silicone rubber chamber connected at each end to silicone rubber catheters. One chatheter has a perforated end which is implanted in the peritoneal cavity of a patient. The other catheter, which extends into the vascular system, is not capable of excluding diffusion and reflux of blood components into the catheter tip. However, should the slightest amount of blood enter the shunt, clotting may occur and occlude the tubing.

To date these two devices are the most used shunting devices for treating patients with ascites. Their use remains limited due to a high incidence of complications, primarily disseminated intravascular coagulopathy (DIC). Studies of peritoneovenous shunt related DIC report that this problem occurs in 100% of the patients. Seventy-four per cent of total complications occur within the first month of implantation, 27% of which are pulmonary complications.

SUMMARY OF THE INVENTION

In the shunt design of the present invention, it is sought to reduce the incidence of DIC primarily by: (a) eliminating the formation of clots inside the catheter tip, thus dramatically reducing the number of microthrombi pumped into the cardiovascular system, and (b) filtering the ascites, thus reducing the amount of fibrinous material from the peritoneal cavity pumped into the cardiovascular system. In addition, device failure due to irreversible catheter clotting, peritoneal drain plugging, and catheter kinking, which occur in 32% of patients, are also addressed by the new design.

Broadly stated, the implantable anti-reflux fluid displacement compression pump-catheter according to this invention consists of three parts, connected by flexible tubing: (1) a double chambered multi-micro-orifice collecting device; (2) an anti-reflux, anti-backdiffusion tubular compression pump; and (3) an anti-reflux, anti-backdiffusion. non-thrombogenic catheter for intravascular placement.

BRIEF DESCRIPTION OF THE DRAWINGS

The invention is illustrated in the accompanying drawings in which corresponding parts are identified by the same numerals and in which:

FIG. 1 is an elevational view of the compression pump-catheter according to the present invention;

FIG. 2 is a longitudinal section on the line 2—2 of FIG. 1 and in the direction of the arrows;

FIG. 3 is a transverse section on the line 3—3 of FIG. 2 and in the direction of the arrows; and FIG. 4 is a transverse section on the line 4—4 of FIG. 2 and in the direction of the arrows.

DETAILED DESCRIPTION OF THE PREFERRED EMBODIMENT

Referring now to the drawings, the compression pump-catheter according to the present invention includes a sieve-like elongated collecting device 10 connected by a catheter or similar length of flexible tubing 11 to a compression pump 12. Pump 12 in turn is connected by a catheter or similar length of flexible tubing 13 to a check valve catheter tip 14.

The ascites collector 10 is constructed from an elongated outer section of flexible tubing 15 and an inner section of flexible tubing 16 of substantially the same length. The tubing sections 15 and 16 are concentrically disposed with an annulus 17 between. Tubing section 15 is provided with a myriad of small diameter perforations 18 to give the tubing section a sieve-like structure. Similarly, the inner tube section 16 is provided with a myriad of small diameter perforations 19.

The distal or upstream end of outer tubing section 15 is closed by a plug closure 20. Similarly, the distal end of inner tubing section 16 is preferably closed by a plug 21. Alternatively, both distal ends of the tubing sections may be closed by a single plug means which also then functions to maintain the concentric arrangement of the tubing sections. The distal end of tubing section 11 is inserted into the proximal or downstream end of inner perforated tubing section 16. A plug 22 serves to close the annulus 17 at the proximal end of the collection device and to connect the collector to tubing 11.

The purpose of constructing a collector which resembles a sieve, rather than one which simply drains ascites through the opening of an unmodified length of rubber tube, is to reduce the probability of plugging of the collecting device either by a loop of bowel, omentum, or fibrin, a common occurrence in both the Le Veen and Newkirk shunts. The use of two concentric sieves adds desirable redundancy to this part of the system.

The compression pump 12 is composed of a length of flexible tubing 23 whose distal end is connected by means of plug 24 to the proximal end of tubing 11 and whose proximal end is connected by means of plug 25 to the distal end of tubing 13. The proximal end of tubing 11 within the chamber defined by tubing 23 is provided with a check valve tip of the type disclosed in Dorman application Ser. No. 245,379, the disclosure of which is incorporated herein by reference.

The proximal end of bore 26 of tubing 11 is closed, as by a short plug 27. One or more cross bore ports 28 are provided in tubing 11 immediately upstream from the plug 27. A thin-walled elastic sleeve 29 is provided over the end of tubing 11 covering ports 28. The upstream end of sleeve 29 is sealed to the tubing by means of an adhesive bond extending around the periphery of the tubing and sleeve. Sleeve 29 is made to a precise fit or undersized, approximately 0 to 30 percent, to generate a fixed compression at the end of the tubing.

The catheter check valve tip 14 at the end of tubing 13 is of similar construction. The proximal end of bore 30 of tubing 13 is closed by means of plug 31. One or more cross bore ports 32 extend through the tubing wall immediately upstream from the plug. Ports 32 are covered by means of thin elastic sleeve 33 which is adhesively attached to the tubing upstream from the cross bore ports. The end of the catheter tip 14 and the end of sleeve 33 may terminate in a plane at an acute angle to the longitudinal axis of the catheter to facilitate entry into a blood vessel.

Preferably, the surfaces adjacent the proximal ends of tubing 11 and 13 and/or the inner surfaces of sleeves 29 and 33 are provided with a thin film glow discharge plasma ploymerized fluorocarbon coating to prevent adhesion of the contacting surfaces, as disclosed in Anderson et al application Ser. No. 422,758, now U.S. Pat. No. 4,536,179, issued Aug. 20, 1985, the disclosure of which is incorporated herein by reference.

The compression pump-catheter shunt is implanted using standard surgical techniques with the collector 10 being located in the peritoneum, the compression pump 12 being positioned in a comfortable and convenient subcutaneous location and the proximal check valve tip 14 being threaded into the desired blood vessel. The shunt is operated by compressing the pumping chamber 12 by hand and releasing. The check valve at the tip of the catheter functions both in preventing reflux of blood components and as the second valve of the pump. When the pumping chamber is compressed, the check valve within the chamber prevents back flow toward the collecting device 10 and causes any ascites fluid already in the pumping chamber to be forced towards the proximal catheter end 14.

The proximal check valve 14 is forced to open as soon as the pressure inside the pumping chamber exceeds the combined forces of the elastic squeeze of the check valve sleeve plus the intravascular blood pressure. When the patient's hand is removed from the pumping chamber 12, the elastic forces within the tubular pump housing cause it to expand to its original shape. This is accompanied by a relative drop in pressure within the pumping chamber. This pressure drop is immediately followed by closing off of the proximal check valve 14 as soon as the pressure within the pumping chamber becomes less than that exerted by the combined elastic sleeve force plus the intravascular blood pressure.

As the pumping chamber pressure decreases to less than that exerted by the intraperitoneal fluid pressure minus the elastic force of the distal check valve, ascites fluid is aspirated into the pumping chamber until the pumping chamber assumes its original shape. At this point, the elastic forces of both check valves and the pumping chamber are all relaxed. This sequence of event is repeated each time the patient compresses and releases the pumping chamber 12. The patient repeats this pumping sequence until substantially all of the ascites is pumped into the cardiovascular system. This end point may be reached either by prescription by the physician or by a self-determined sensory end point.

All of the components of the compression pump-catheter shunt system are formed from any of a number of available flexible inert non-toxic bio-compatible rubber or synthetic rubber-like materials. A preferred material for the tubing components is medical grade silicone rubber tubing and a preferred material for the several plugs and connections is medical grade Silastic adhesive. A preferred material for check valve sleeves 29 and 33 is silicone rubber with the sleeve separated from the rest of the catheter by a film of low surface energy material, such as polytetrafluoroethylene (Teflon).

Dimensions are not critical, the compression pumpcatheter system being sized to meet particular needs. In one exemplary system, collector 10 was constructed from two approximately 10 inch lengths of silicone rubber tubing. Outer tubing section 15 had an outer diameter of 0.69 inch and an inner diameter of 0.50 inch.

Inner tube section 16 had an outer diameter of 0.31 inch and an inner diameter of 0.19 inch. Both sections of tubing were perforated with several hundred 0.04 inch diameter holes.

Catheter tubing 11 may be approximately 6 to 12 inches long. The length of the proximal catheter 13 may range from 12 to 24 inches depending upon the anatomy of the patient of the shunt. Acceptable cross-sectional catheter dimensions for both tubing 11 and 13 range from 0.08 to 0.25 inch outer diameter, with at least an 0.04 inch inner diameter, and an inner to outer diameter ratio of greater than 1.7:1 when using Silastic medical grade silicone tubing. Optimized dimensions are approximately 0.125 inch outer diameter and 0.062 inch inner diameter, with a ratio of 2.0:1.

Although the exact dimensions of this tubing are not critical, several criteria must be met in order to achieve optimized performance. The inner to outer diameter ratio must be such that given an inner lumen or bore which does not significantly add resistance to pumping of ascitic fluid, the outer diameter must be such that the wall thickness is great enough so that the tubing resists kinking when it is bent to a degree likely to be encountered during surgical implantation. At the same time, the outer diameter must not be so large that the tubing resists the types of bends that are necessary for implantability.

The outer diameter of the proximal check valve tip 14 must be small enough to be tolerated by the vein in which it is inserted. Elastic sleeves 29 and 33 may be about 0.0005 to 0.01 inch thick. The proximal check valve 14 and that within the compression pump 12 need not have identical dimensions.

By manufacturing the check valves with low elastic forces of less than 20 cm of water, combined operating pressure, it is possible to produce a passive shunt. This passive shunt requires no manual compressive pumping in order to drain ascites. Instead, ascites drains automatically any time pressure in the peritoneum exceeds venous pressure, plus the elastic squeeze of the sleeve, plus the hydrostatic pressure head due to the difference in elevation between the proximal catheter tip 14 and the collector 10.

It is apparent that many modifications and variations of this invention as hereinbefore set forth may be made without departing from the spirit and scope thereof. The specific embodiments described are given by way of example only and the invention is limited only by the terms of the appended claims.

We claim:

1. An implantable anti-reflux fluid displacement compression pump-catheter system which comprises:
   (A) a double chambered multi-orifice collecting device including:
      (1) a first elongated flexible inner tube having a plurality of several hundred small perforations,
      (2) a second elongated flexible outer tube of substantially the same length as the first tube surrounding the first tube and substantially concentric therewith, said outer tube having a plurality of several hundred small perforations,
      (3) plug means at the distal end of the device closing the ends of the tubes, and
      (4) further plug and spacer means at the opposite end of the device closing the end of the outer tube, maintaining the tubes in concentric relationship and connecting the collecting device to tubing extending to the pump,
   (B) an anti-reflux anti-backdiffusion tubular compression pump including:
      (1) an elongated resilient tubular housing,
      (2) the proximal end of the tubing connecting said collecting device fixed substantially concentrically in the distal end of said housing and extending into the housing,
      (3) plug and spacer means closing the distal end of the pump housing, maintaining the housing and tubing in concentric relationship and connecting the pump to said tubing,
      (4) a check valve tip at the end of said tubing, said valve tip comprising:
         (a) a closure at the proximal end of said tubing extending into the pump housing,
         (b) at least one port in the wall of the tubing communicating with the bore of the tubing, said port being located upstream from the closed end of the tubing and closely adjacent thereto,
         (c) a thin elastic sleeve surrounding the closed end of said tubing in squeezing engagement therewith, said sleeve covering said port, and
         (d) means securing the distal end of said sleeve to the tubing upstream from the port,
      (5) the distal end of the tubing connecting said pump to said catheter fixed substantially concentrically in the proximal end of said pump housing, and
      (6) plug and spacer means closing the proximal end of the pump housing, maintaining the housing and tubing in concentric relationship and connecting the pump to said tubing, and
   (C) an anti-reflux anti-backdiffusion non-thrombogenic catheter having a check valve tip and including:
      (1) an elongated relatively thick-walled tubular member,
      (2) a central bore in said member, said bore being open at the distal end and closed at the proximal end,
      (3) at least one port in the wall of the tubular member communicating with said bore, said port being located upstream from said closed proximal end of the tubular member closely adjacent thereto,
      (4) a thin elastic sleeve surrounding said tubular member in squeezing engagement therewith, said sleeve convering said port, and
      (5) means securing said sleeve to the tubular member upstream from the port.

2. An implantable anti-reflux fluid displacement compression pump-catheter system according to claim 1 wherein the proximal end of the sleeve and the closed proximal end of the check valve tip of said compression pump terminate in a plane transverse to the longitudinal axis of the tubing to provide a high velocity jet port.

3. An implantable anti-reflux fluid displacement compression pump-catheter system according to claim 1 wherein the proximal end of the catheter tip and the end of the sleeve thereof terminate in a plane at an acute angle to the longitudinal axis of the catheter.

4. An implantable anti-reflux fluid displacement compression pump-catheter system according to claim 1 wherein the components of the system are formed from medical grade silicone rubber.

5. An implantable anti-reflux fluid displacement compression pump-catheter system according to claim 1 wherein at least one of the surfaces of the elastic sleeve of both of said check valve tips or the tubular wall underlying the sleeve is provided with a thin film glow discharge plasma polymerized fluorocarbon coating to prevent adhesion of the contacting surfaces.

6. An implantable anti-reflux fluid displacement compression pump-catheter system which comprises:
   (A) an elongated double chambered multi-micro-orifice tubular collecting device,
   (B) an anti-reflux anti-backdiffusion, tubular compression pump,
   (C) an anti-reflux anti-backdiffusion non-thrombogenic catheter, and
   (D) flexible tubing connecting said collecting device and pump and said pump and catheter in series, wherein the pump of said system comprises:
      (1) an elongated resilient tubular housing,
      (2) the proximal end of the tubing connecting said collecting device fixed substantially concentrically in the distal end of said housing and extending into the housing,
      (3) plug and spacer means closing the distal end of the pump housing, maintaining the housing and tubing in concentric relationship and connecting the pump to said tubing,
      (4) a check valve tip at the end of said tubing, said valve tip comprising:
         (a) a closure at the proximal end of said tubing extending into the pump housing,
         (b) at least one port in the wall of the tubing communicating with the bore of the tubing, said port being located upstream from the closed end of the tubing and closely adjacent thereto,
         (c) a thin elastic sleeve surrounding the closed end of said tubing in squeezing engagement therewith, said sleeve covering said port, and
         (d) means securing the distal end of said sleeve to the tubing upstream from the port,
      (5) the distal end of the tubing connecting said pump to said catheter fixed substantially concentrically in the proximal end of said pump housing,
      (6) plug and spacer means closing the proximal end of the pump housing, maintaining the housing and tubing in concentric relationship and connecting the pump to said tubing, and
      (7) further check valve means downstream from said check valve tip.

7. An implantable anti-reflux fluid displacement compression pump-catheter system according to claim 6 wherein the proximal end of the sleeve and closed proximal end of the check valve tip terminate in a plane transverse to the longitudinal axis of the tubing to provide a high velocity jet port.

8. An implantable anti-reflux fluid displacement compression pump-catheter system which comprises:
   (A) an elongated double chambered multi-micro-orifice tubular collecting device,
   (B) an anti-reflux anti-backdiffusion, tubular compression pump,
   (C) an anti-reflux anti-backdiffusion non-thrombogenic catheter, and
   (D) flexible tubing connecting said collecting device and pump and said pump and catheter in series, wherein said catheter has a check valve tip and comprises:
      (1) an elongated relatively thick-walled tubular member,
      (2) a central bore in said member, said bore being open at the distal end and closed at the proximal end,
      (3) at least one port in the wall of the tubular member communciating with said bore, said port being located upstream from said closed proximal end of the tubular member and closely adjacent thereto,
      (4) a thin elastic sleeve surrounding said tubular member in squeezing engagement therewith, said sleeve covering said port, and
      (5) means securing said sleeve to the tubular member upstream from the port.

9. An implantable anti-reflux fluid displacement compression pump-catheter system according to claim 8 wherein the proximal end of the catheter tip and the end of the sleeve thereof terminate in a plane at an acute angle to the longitudinal axis of the catheter.

* * * * *